United States Patent [19]
Beasley et al.

[11] Patent Number: 5,152,887
[45] Date of Patent: Oct. 6, 1992

[54] PROCESS FOR RECLAIMING WASTE GAS TREATMENT CHEMICAL

[76] Inventors: Todd Beasley, 610 Prairie Meadows Close, Brooks, ALberta, Canada, T0J 0J0; Dwight A. Merritt, 610 Lake Simcoe Close SE., Calgary, ALberta, Canada, T2J 5H2

[21] Appl. No.: 835,076

[22] Filed: Feb. 18, 1992

Related U.S. Application Data

[63] Continuation of Ser. No. 433,159, Sep. 13, 1990, abandoned.

[51] Int. Cl.⁵ .................. B01D 3/10; C07C 209/84
[52] U.S. Cl. ............................ 203/22; 203/37; 203/47; 203/87; 203/94; 203/100; 423/229; 564/497
[58] Field of Search ............ 203/22, 23, 87, 37, 203/41, 47, 94, 98, 100, 91, DIG. 91, DIG. 11, 14; 202/180, 153, 177, 202, 159, 178, 198; 564/497; 423/226–229; 159/46, 47.3

[56] References Cited

U.S. PATENT DOCUMENTS

| | | | |
|---|---|---|---|
| 2,159,621 | 5/1939 | Van Dijck | 203/DIG. 11 |
| 2,619,453 | 11/1952 | Andersen | 203/99 |
| 2,892,775 | 6/1959 | Anderson | 564/497 |
| 3,073,752 | 1/1963 | Mention | 203/22 |
| 3,234,109 | 2/1966 | Lustenader | 203/22 |
| 3,294,650 | 12/1966 | Manteutel | 203/22 |
| 3,388,046 | 6/1968 | Hendrix | 203/22 |
| 3,506,543 | 4/1970 | Hayes et al. | 202/202 |
| 3,532,606 | 10/1970 | Sibert | 203/10 |
| 3,658,462 | 4/1972 | Van Scoy | 423/229 |
| 4,045,293 | 8/1977 | Cooksley | 202/202 |
| 4,152,217 | 5/1979 | Eisenberg | 203/DIG. 9 |
| 4,548,620 | 12/1985 | Albiol | 423/228 |
| 4,798,654 | 1/1989 | Iimura et al. | 203/94 |
| 4,798,910 | 1/1989 | Herrin | 564/497 |
| 4,808,344 | 2/1989 | Hallenburg et al. | 203/94 |
| 4,975,154 | 12/1990 | Palmer et al. | 202/202 |

*Primary Examiner*—Wilbur Bascomb, Jr.

[57] ABSTRACT

When regenerating gas treating chemicals such as diethanolamine solution, the usual practice is to subject the chemicals to steam stripping. Ultimately such action is ineffective, and it is necessary to discard the chemicals. The waste chemical can be reclaimed by preheating the chemical in a countercurrent heat exchanger, in which heat is recovered from an already processed product; using a still to separate the preheated, partially vaporized chemical from the remainder of the chemicals; i.e. impurities or still bottoms; heating the still bottoms and recycling such bottoms for mixing with the partially vaporized chemical immediately upstream of the still; returning the separated vapor product from the still to the heat exchanger for heating feed chemical; and separating the thus partially condensed product in a separator to yield reclaimed gas treating chemical.

16 Claims, 7 Drawing Sheets

PROCESS FOR RECLAIMING WASTE GAS TREATMENT CHEMICAL

This application is a continuation of application Ser. No. 07/433,159, filed Sep. 13, 1990, now abandoned.

BACKGROUND OF THE INVENTION

This invention relates to a process and an apparatus for purifying and recovering waste gas treating chemicals.

Waste gas treating chemicals such as alkanolamines, are used in aqueous solution which flows countercurrent to natural gas for removing acid gases such as hydrogen sulfide and carbon dioxide, and/or water vapor from the gas. Thereafter, the gas treating chemical flows countercurrent through steam in a regenerator or stripper in order to remove absorbed material from the treating chemicals. Over a period of time, certain contaminants accumulate in the solution. When the contaminant level is such that the solution is no longer effective for removing acid gases, or when the removal of such acid gases and regeneration becomes too expensive or too corrosive, the gas treating chemical must be replaced.

The contaminants commonly found in the gas treating chemicals include products of the thermal degradation of the gas treating chemicals, heat stable salts, asphaltenes, light hydrocarbons, suspended solids or combinations thereof. The degradation products are high boiling nitrogen and oxygen compounds, and the heat stable salts include sodium thiosulphate, sodium thiocyanate and sodium sulphide. In order to reclaim the gas treating chemical, it is necessary to remove all such impurities.

However, when attempting to reclaim gas treating chemicals, it must be understood that all gas treating chemicals are susceptible to decomposition at elevated temperatures, and any attempt to remove impurities at a temperature of 400° F. or higher will result in thermal decomposition of the gas treating chemical. The temperature of 400° F. has been established as the temperature above which decomposition becomes measurable. Moreover, most gas treating chemicals are corrosive, which condition is exacerbated by high temperatures and long residence times in the reclaiming apparatus.

An example of a waste gas treating chemical reclaiming process is found in U.S. Pat. No. 2,914,469, which issued to H. M. Anderson et al on Nov. 24, 1959. The Anderson et al method uses potassium hydroxide which is added to a contaminated diethanolamine solution to form an eutectic mixture of molten salt. The process is carried out at atmospheric pressure and at a temperature of from 450° to 460° F.

OBJECTS OF THE INVENTION

An object of the present invention is to provide a process and an apparatus for removing virtually all impurities from a waste gas treating chemical, permitting a 90-95% recovery of the chemical from the waste solution.

Another object of the present invention is to provide a process which operates at a relatively low temperature, thus minimizing the formation of additional decomposition products and reducing the likelihood of corrosion.

Yet another object of the invention is to provide a process which reduces the likelihood of corrosion by maintaining the chemicals being treated at a pH of 8 or higher, if necessary by the addition of a base.

BRIEF SUMMARY OF THE INVENTION

According to one aspect the invention relates to a process for recovering waste gas treating chemical comprising the steps of:
 (a) preheating said treating chemical in an at least partial vacuum to at least partially vaporize the chemical;
 (b) heating the partially vaporized chemical in a high vacuum to separate product vapor from the remainder of the treating chemical;
 (c) heating a portion of the remaining treating chemical;
 (d) mixing said heated treating chemical with said partially vaporized chemical to effect said heating step (b); and
 (e) recovering said separated product vapor.

In accordance with another aspect, the invention relates to an apparatus for recovering waste gas treating chemical comprising:
 (a) preheat means for preheating said treating chemical in an at least partial vacuum;
 (b) still means for heating the partially vaporized chemical in a vacuum to separate product vapor from the remainder of the treating chemical;
 (c) heater means for heating at least a portion of the remainder of the treating chemical; and
 (d) mixer means for mixing heated treating chemical with said partially vaporized chemical and for feeding the mixture thus produced into said still means.

DESCRIPTION OF THE DRAWINGS

The invention will be described in greater detail with reference to the accompanying drawings, which illustrate a preferred embodiment of the invention, and wherein.

DESCRIPTION OF THE PREFERRED EMBODIMENTS

Figure 1A:
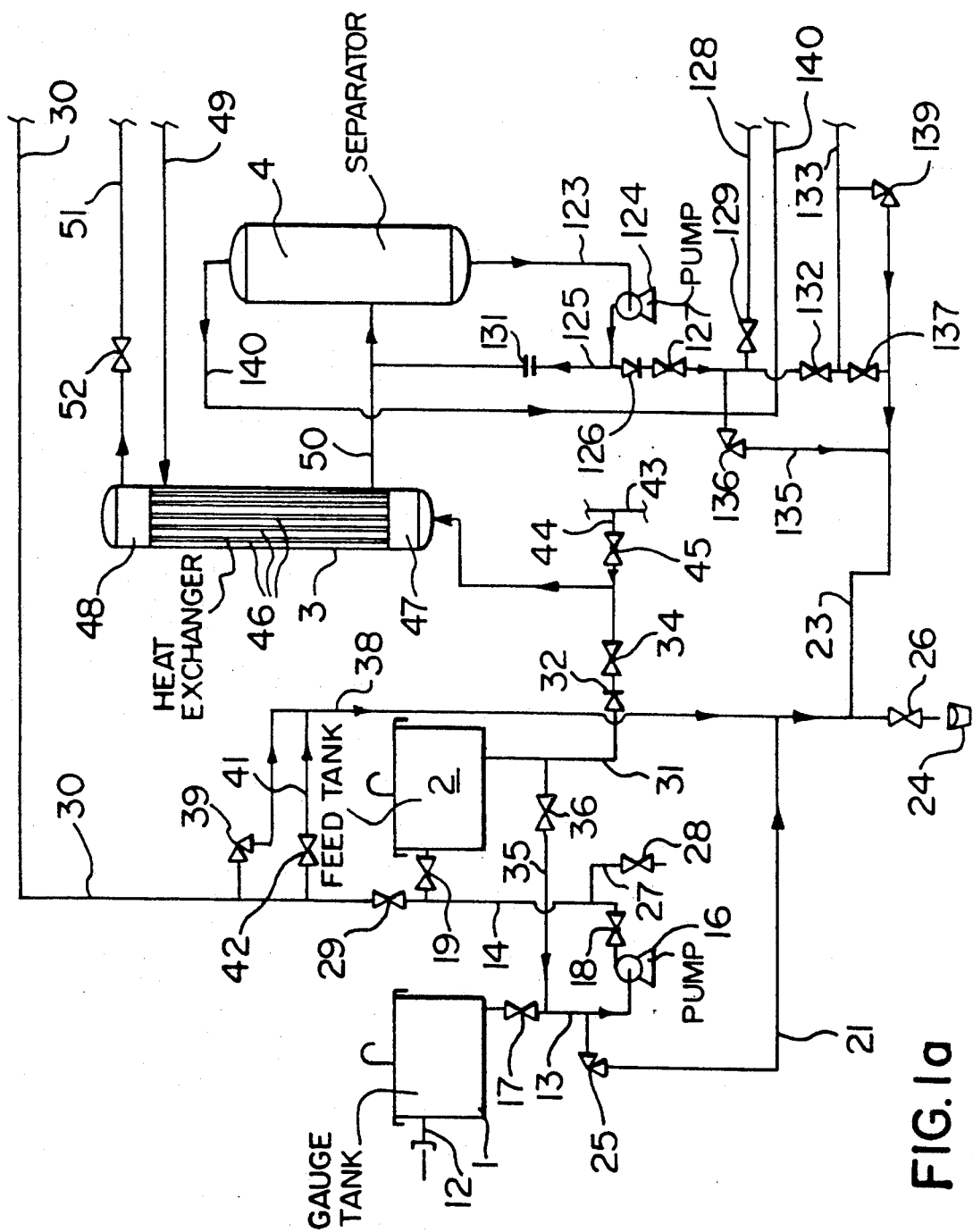
FIGS. 1a, 1b and 1c of which combine together to form a single schematic flow diagram of a preferred embodiment of an apparatus in accordance with the present invention.

For the sake of simplicity, the following detailed description of the method and apparatus is limited to the treatment of a diethanolamine solution (DEA). It will be appreciated that the feed may also be triethylene glycol, or other chemicals such as mono- or diethylene glycol, methyl diethanolamine, sulfolane or sulfinol.

The main elements of the apparatus of the invention include a gauge tank 1, a feed tank 2, a heater exchanger 3, a separator 4, a still 5, a heater 6, a condenser 7, a solvent cooler 8, a filter 9 and a water cooler 10.

Waste diethanolamine solution is fed into the apparatus under pressure. The solution enters the gauge tank 1 through an inlet pipe 12. The tank 1 operates at atmospheric pressure and at a temperature of 40°-75° F. The tank 1 is intended to receive the solution, so that the quantity can be measured using a liquid level gauge (not shown). The apparatus operates on a batch basis. The levels in the tank 1 and the following feed tank 2 are monitored. When the level in the gauge tank 1 nears the top of the tank, and the level in the feed tank 2 is low enough to receive the contents of the tank 1, the operator transfers the contents of the tank 1 to tank 2 through lines 13 and 14, pump 16 and valves 17, 18 and 19. A line 21 intersects the line 13 upstream of the pump 16 for carrying the contents of the line 13 to a drain header 23 and a receiver 24. A safety relief valve 25 is provided in the line 21, and a drain valve 26 is provided in the header 23. An outlet duct 27 with a valve 28 is provided in the line 14 downstream of the valve 18, permitting the withdrawal of samples for analysis.

During start-up operations, the valve 19 remains closed, and a valve 29 in a pipe 30 is opened to feed solution to the still 5. Feed from the tank 1 to the tank 2 is initiated manually when the operator observes that the level in the tank 2 has fallen to a level where it can accept fresh change of solution from the tank 1.

The tank 2 operates at atmospheric pressure and at a temperature of 40°-75° F. No pump is required for feeding solution downstream from the tank 2, because the other elements operate under a high vacuum of 16-28" of mercury, and flow is caused by pressure differentials between the tank 2 and such downstream elements. The feed tank 2 prevents surging, ensuring a constant flow rate in the apparatus. Flow from the tank 2 through passes line 31 and a one-way valve 32, and is controlled by a manually operated valve 34. A bypass line 35 with a valve 36 extends from the line 31 to the line 13 for draining the contents of the tank 2 through the lines 13 and 21, and the drain header 23. A line 38 with a safety relief valve 39 also connects the start-up line 30 to the drain header 23. A bypass 41 with a valve 42 connects the line 30 to the line 38 for manually effecting draining of the line 30 when the apparatus is shut down or the line 30 is not in use. The line 31 can be connected to a nitrogen purge header 43 by a line 44 and a valve 45.

Solution flowing from the tank 2 through the line 31 to the heat exchanger 3 enters the bottom of the latter. The solution enters the tubeside of the heat exchanger 3, which includes a plurality of tubes 46 extending between inlet and outlet chambers 47 and 48, respectively. During passage through the tubes 46, the solution is heated by vapors flowing countercurrent through the shell or casing of the heat exchanger 3. The vapors flow from the still 5 via line 49 to the top end of the heat exchanger 3, and are discharged therefrom through pipe 50 to the separator 4.

The solution flowing through the tubes 46 is heated to approximately 127° F. and partially vaporized and is discharged from the outlet chamber 48 through a line 51 and a valve 52 to a mixer 53. The vapors from the still 5 are cooled to approximately 133° F. during passage through the heat exchanger 3 and partially condensed. The controlled condensation of the DEA solution, facilitates the removal of water and light impurities from the solution. Moreover, the heat exchanger 3 recovers heat which otherwise would have to be added to the system, and such heat would later have to be removed by water cooling at additional expense. The valve 52, which is manually actuated, controls the degree of condensation and product composition. The valve 52 causes a pressure drop of from 0 to 9 psi between the atmospheric pressure in the feed tank 2 and the high vacuum of 26-27" of mercury in the still 5. Thus, the outlet pressure of the feed from the heat exchanger 3 can be controlled (a vacuum from 23 to 10" of mercury) which directly affects the quantity of heat exchanged and the condensation of product vapors. The product separator 4 will be described hereinafter in greater detail. The partially vaporized feed solution from the heat exchanger 3 flows through the line 51 and the valve 52 to the mixer 53 where the solution is mixed with bottoms from the still 5. Such bottoms are discharged through an outlet duct 60, a pump 61, a one-way valve 62, a valve 64 and a line 66 to the heater 6. A bypass 68 with a valve 69 therein is used in the event of a shutdown to drain the coil 70 in the heater 6 into the still 5. A line 72 with a solenoid operated valve 73 is connected to the line 66 and to the nitrogen purge header 43. The valve 73 is normally closed during operation of the apparatus. In the event of a power failure, a spring (not shown) in the valve opens the latter to connect the line 66 to the purge header 43, thus blowing the contents of the heater 6 into the still 5. The bottoms pass through the heater 6 and are returned to the mixer 53 via a line 75.

During start-up, the still 5 is charged with solution entering through the line 30, a one-way valve 76 and a control valve 77. A hose connection 79 is provided in the line 30 for admitting nitrogen for purging and flushing the system. Caustic soda and anti-foaming agents are added to the recirculated bottoms immediately prior to the mixer 53. The caustic soda and anti-foaming agent are fed from containers 81 and 82 via lines 83 and 84, manually operated valves 85 and 86 and lines 30 and 75 into the mixer 53.

The bottoms entering the mixer 53 are approximately 15% DEA and 1% water, the remainder being heavy impurities. The bottoms are heated to 390° F. in the heater 6. The bottoms flow to the mixer 53, which is used to heat and thus complete the vaporization of the DEA solution and vapors from the heat exchanger 3. This is effected during an extremely short residence time and with thorough mixing of the various ingredients. The mixer 53 has a tangential bottoms entry to a main feed pipe. Mixing vanes or baffles in the main pipe ensure thorough mixing of the streams. The feed for the still 5 is changed from a partially to a fully vaporized state quickly in order to avoid degradation. The caustic soda is added to diethanolamine feedstock to free the amine, which may be held in a heat stable salt, and to raise the pH to at least 8.0 for reducing corrosion. The antifoaming agent is added as required to eliminate foam in the still 5. The quantity of heat and the resulting outlet temperature of the DEA from the mixer 53 are controlled by adjusting the temperature of the recirculated bottoms. This temperature is the most important single variable in the apparatus.

The still 5 receives the mixture produced in the mixer 53 through line 87, and separates such mixture into a vapor which is returned to the heat exchanger 3 for condensation, and bottoms which constitute waste. Most of the bottoms are recirculated through the heater 6 and returned to the mixer 53. The still 5 is designed to separate vapor and liquid. The mixture from the mixer 53 is fed through a "wiping" type entrance followed by a low velocity section with sufficient residence time that the vapor flow enhances liquid separation. The still 5 operates with a minimum liquid level which is normally contained in a boot 88 beneath the main body of the still casing.

The pump 61 is used to transfer liquid still bottoms to the heater 6, and excess bottoms through line 90, one-way valve 91 and control valve 92 to waste drums (not shown). A vent 93 to atmosphere containing a pressure operated safety valve 94 is provided on the still 5. A hose connection 95 is provided in the line 90 for purging of the system. An outlet duct 96 with a valve 97 is also provided in the line 90 permitting the removal of samples for analysis. The pump 61 transfers waste bottoms from the still 5 under vacuum to the heater 6 and to disposal, both under pressure. No control or discharge throttling is provided on the flow through the pump 61 to ensure that maximum flow is always maintained and through the heater 6.

Figure 2:
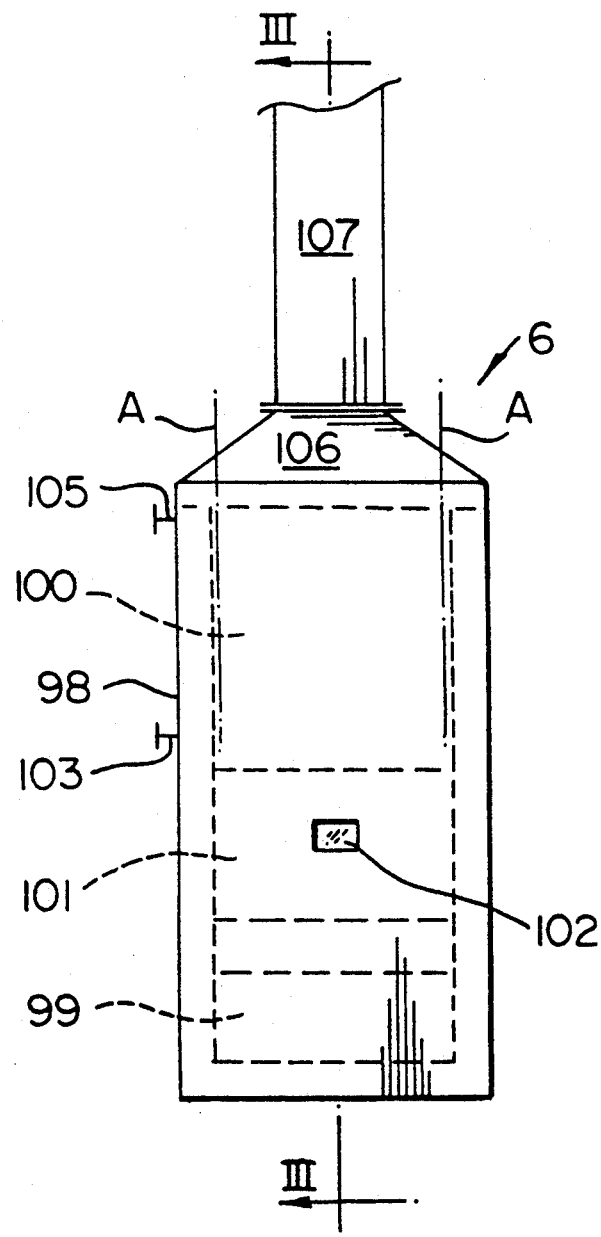
FIG. 2 is a schematic end view of a heater used in the apparatus of FIG. 1.
Figure 3:
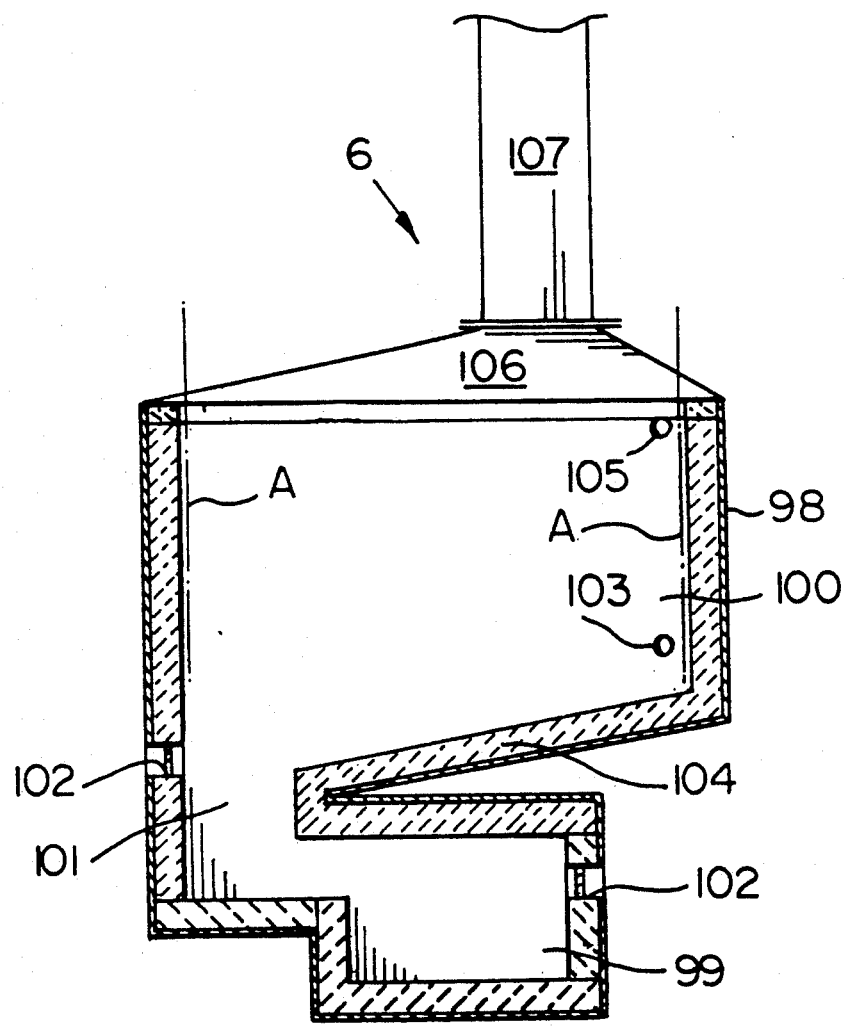
FIG. 3 is a cross section taken generally along line III—III of FIG. 2.
Figure 4:
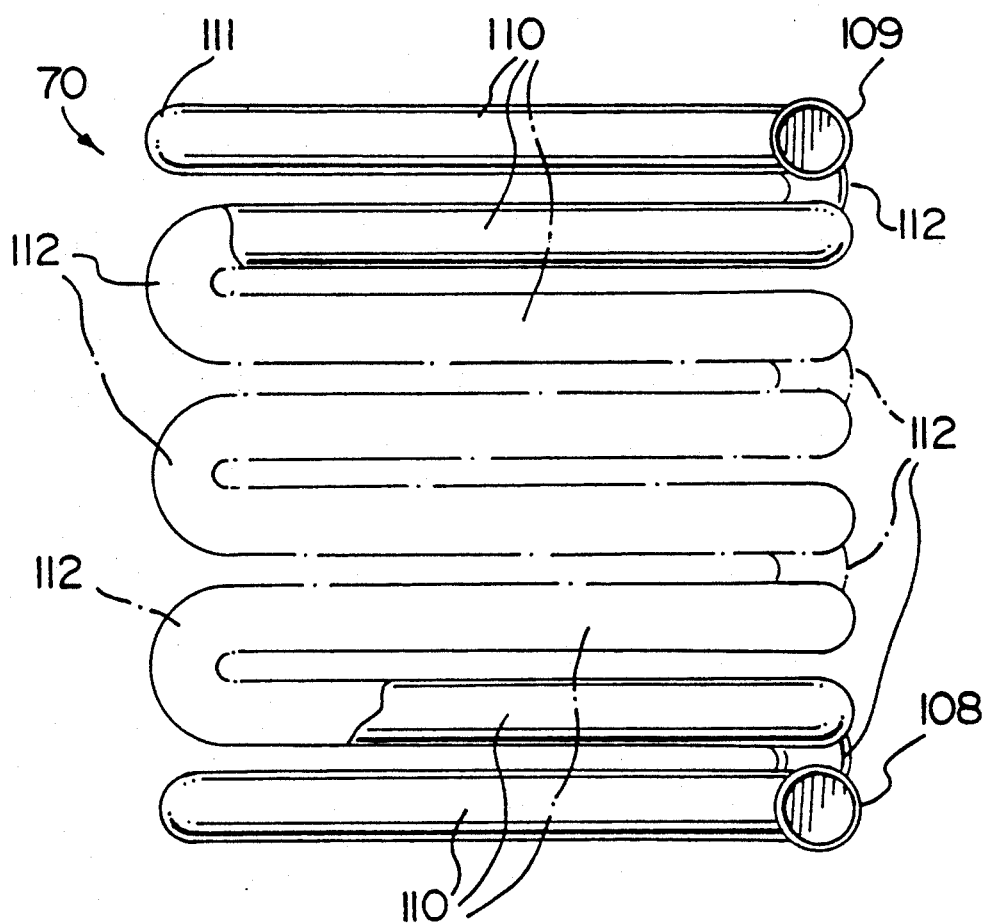
FIG. 4 is a side elevational view of a heater coil used in the heater of FIGS. 2 and 3.
Figure 5:
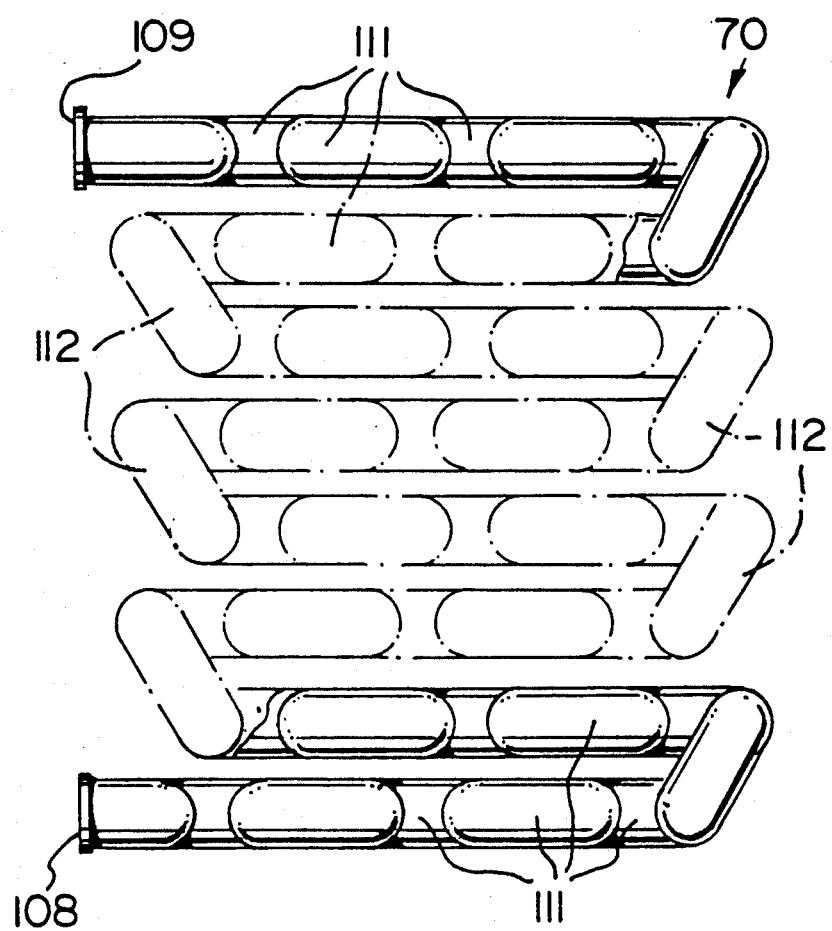
FIG. 5 is an end view of the heater coil of FIG. 4.

Referring to FIGS. 2 and 3, the heater 6 includes a thick steel casing 98 lined with refractory material defining a bottom section or firebox 99 for receiving a burner (not shown) and a top or coil section 100 for receiving the coil 70 (FIGS. 4 and 5). The firebox 99 and the coil section 100 are separated by a neck portion 101, so that there is no contact between the flame in the firebox 99 and the coil 70. Sight ports 102 are provided in the firebox 99 and in the neck portion 101 of the casing. A coil inlet opening 103, i.e. and inlet to the coil 70, is provided above the inclined wall 104 of the coil section 100, and a coil outlet 105 is provided near the upwardly tapering top wall 106 of the casing. A hinged stack 107 carries flue gases from the casing 98. The stack 107 carries flue gases from the casing 98. The stack 107 is located at the end of the casing opposite to the neck portion 101 so that hot gases must flow across the coil 70 before being exhausted from the heater 6.

The tube bundle defining the coil 70 fills most of the coil section 100 of the casing 98. The area of the tube bundle is delineated by broken lines A in FIGS. 2 and 3. The coil 70 (FIGS. 4 and 5) defines a serpentine path through the top section 100 of the casing 98 from a bottom inlet end 108 to a top outlet end 109. The coil 70 includes a plurality of straight sections 110 interconnected at the ends by semicircular connectors 111. At the end of each horizontal row of sections 110 a semicircular connector 112 rises to the next superjacent row of sections 110.

The heater 6 heats the waste bottoms in a one-pass flow from an inlet temperature of 360° F. to an outlet temperature of 390° F. There is no other heat source for such bottoms. At the heater outlet, less than 1% of the feed is vaporized. Thus, the walls of the heater tubes are continuously covered with liquid. The heater firebox 99 receives natural gas from a source thereof via line 114, solenoid valve 115 and control valve 116. The firebox 99 also acts as a combustion site for waste gases fed from the bottom of condenser 7 via line 117, a vacuum pump 118, line 119, one-way valve 120, solenoid-operated valve 121 and flame arrester 122. The heater 6 provides the heat input for the apparatus and burns waste gases from the vacuum pump 118, converting the gases to less noxious substances. The products of combustion are discharged via the stock 107.

The design and operation of the heater 6 are important in order to prevent degradation of the DEA product. The use of a vacuum in the still 5 permits vaporization of the DEA at a temperature below that at which decomposition starts. The quantity of bottom waste flowing to the heater 6 and the velocity of waste liquid in the heater tubes (six to ten ft./second) ensure (i) that the heater outlet temperature is less than 400° F., (ii) that outlet vaporization is less than 1%, (iii) that the maximum tube wall temperature is less than 410° F., and (iv) that the residence time of waste liquid in the heater 6 is from 30 to 60 seconds. All of these factors minimize the temperature to which the waste is exposed, and the time of such exposure. There is no direct heat transfer from the burner flame to the waste liquid in the heater 6, heating being effected by convection only. Thus, heat transfer is limited to approximately 5,000 BTU/h/ft$^2$. There is no direct flame contact with the heater tubes.

The product vapor separated from the bottoms (liquid) in the still 5 is returned to the product separator 4 (FIG. 1a) via the line 49, the heat exchanger 3 and the line 50. Thus, partially condensed DEA (the product) from the heat exchanger 3 is fed to the separator 4. The liquid, which is the purified product, is separated from the vapor, which is essentially all water vapor. The separated liquid is discharged through a line 123 and pump 124 to a line 125 and through a one-way valve 126, a control valve 127, a line 128 and a valve 129 for further treatment in the solvent cooler 8 (FIG. 1c) as described hereinafter in greater detail. The line 50 is also connected to the line 125 through a restricted orifice 131, which passes minimum flow for pump 21 through the line 125. Start-up condensate flows through the valves 126 and 127, a valve 132 and a line 133 to product water storage (not shown). A line 135 containing a safety relief valve 136 connects the line 125 to the drain header 23. The line 125 is also connected through a valve 137 downstream of the valve 132 and the line 133 to the drain header 23. The line 133 is also connected by a safety valve 139 to the drain header 23. The water vapor discharged from the top of the separator 4 is fed through line 140 to the top of the condenser 7 (FIG. 1c).

The product or solvent is pumped to the solvent cooler 8 under sufficient pressure to deliver the product to the user. The warm product at 130° F. flows to the outer tube of the co-axial tube, countercurrent flow cooler 8. The cooler 8 reduces the temperature of the product to a level which is safe to handle and deliver to the user. The cooled product then passes through line 142 and valve 143 into the filter 9, or directly through a valve 145 to a product discharge line 146. The product is discharged from the filter 9 through a line 148 and a valve 149 to the line 146. Samples for analysis can be removed from the line 146 through valve 150.

Warm vapor and non-condensibles from the separator 4 enter the top of the condenser 7 via line 140 at a temperature of approximately 130° F. These substances flow through tubes 152, cooling to approximately 90° F. and condensing. Cooling water for the condenser 7 enters the bottom of the condenser casing through a line 153, valve 154, line 156, pump 157 and line 158 connected to a reservoir or tank 160. The tank 160, lines 156 and 158, and pump 157 also supply the cooler 8 via valve 161 and line 162. A bypass 164 containing a valve 165 extends between the line 162 and the tank 160. Water passing through the condenser 7 is discharged through a line 167 and fed to the water cooler 10. The water cooler 10 includes a fan 168 and an inlet tube 170 containing spray orifices. The cooler 10 is connected by line 171 to the water tank 160. A heater 173 in the tank 160 is used to prevent freezing during start-up and shut down operations.

Figure 1B:
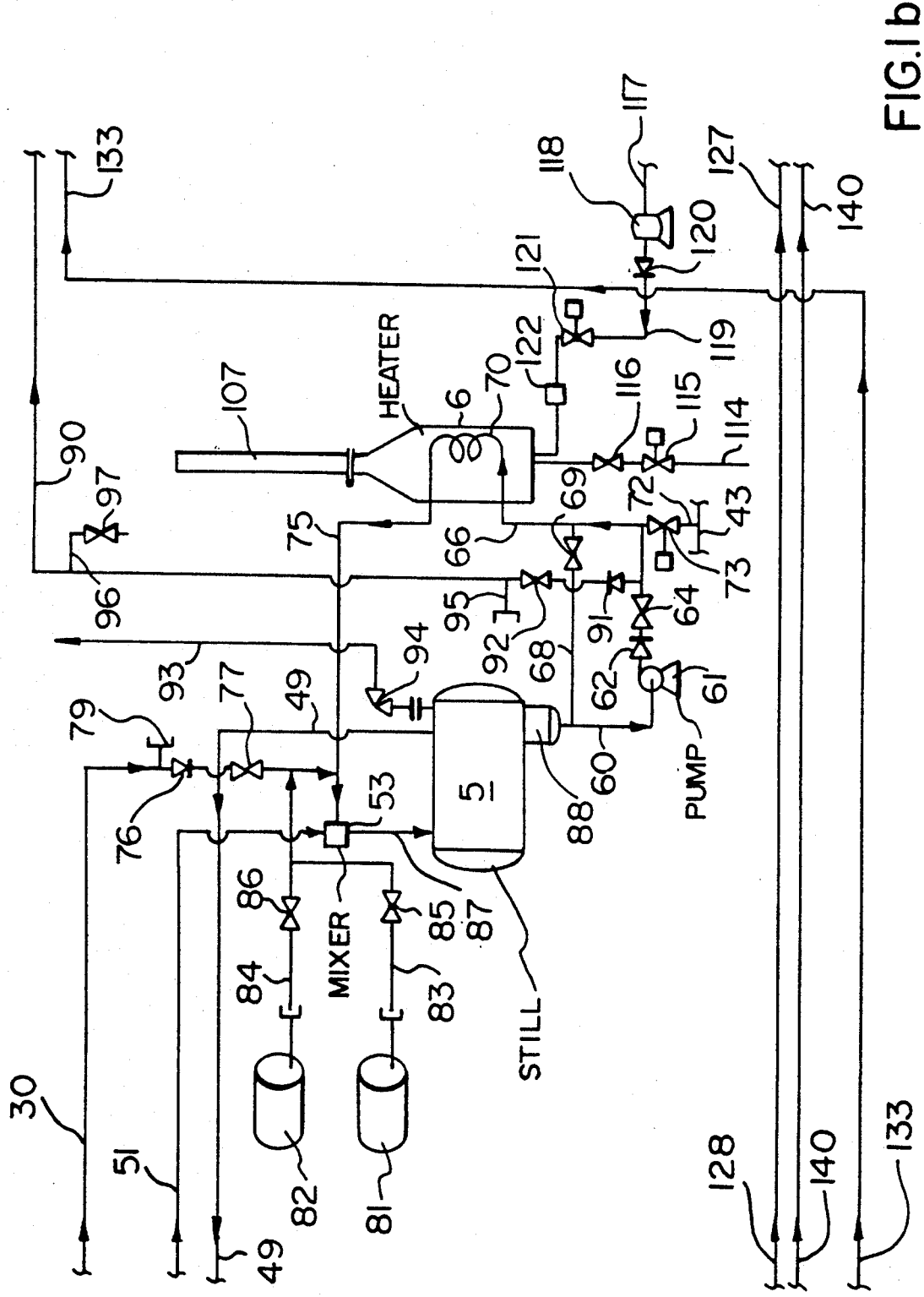
Figure 1C:
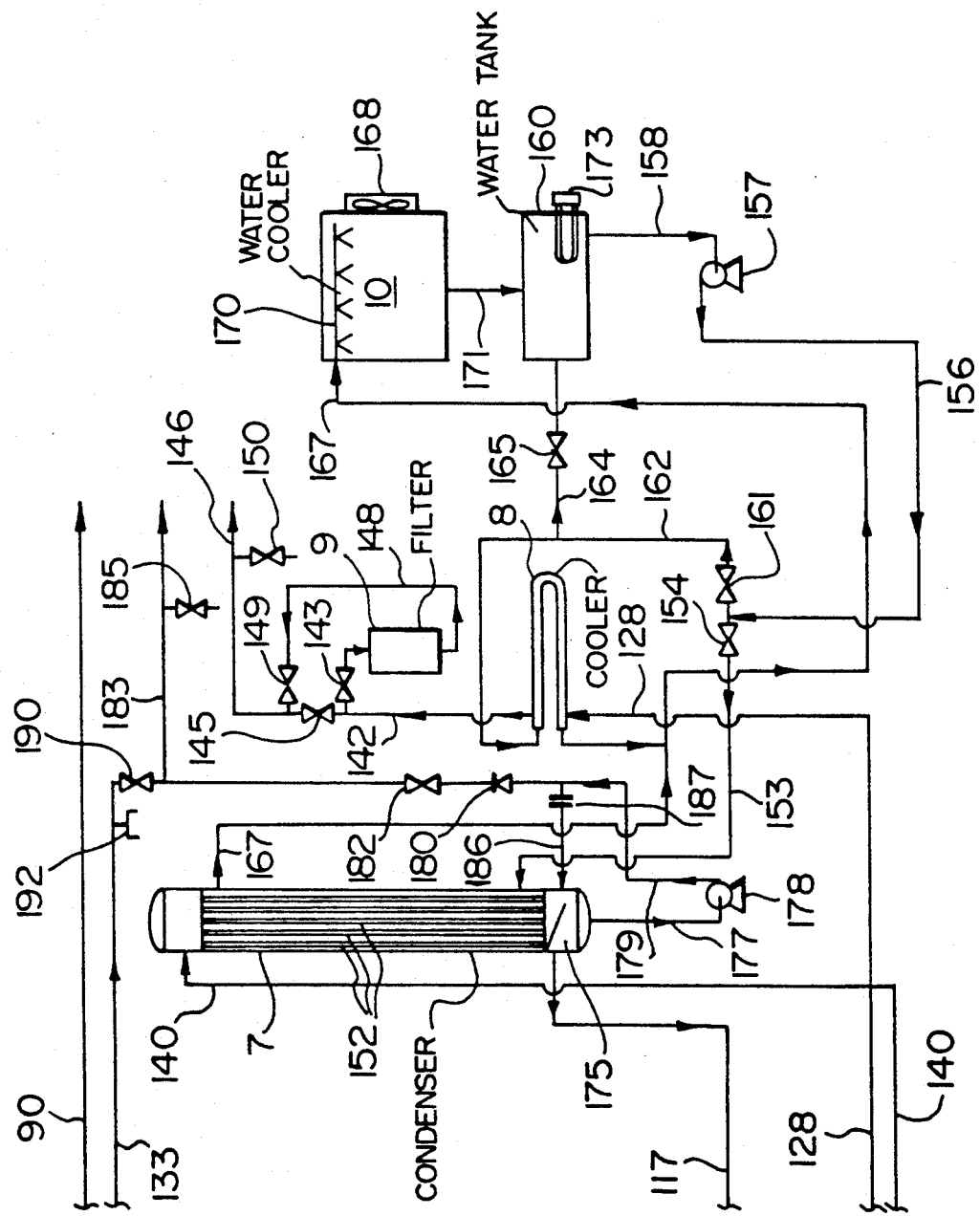

Non-condensible gases are separated from condensed water in the bottom head 175 of the condenser 7, and flow through line 117 to the vacuum pump 118 (FIG. 1b). The condensed water, after separation in the bottom head 175 flows through line 177, condensate pump 178, line 179, one-way valve 180 and control valve 182 to a discharge line 183, which is used to discharge the condensate to disposal. A sample can be removed from the discharge line 183 through valve 185 for analysis. The line 179 is connected to the bottom head 175 of the condenser 7 by a line 186 and a restricted orifice 187, which ensures a minimum flow through the pump 178 at all times and recirculation to suction.

During start-up, start-up condensate is passed through line 133 from line 123 and the separator 4 through a valve 190 into the downstream end of the condenser system. A hose connection 192 is provided in the line 133 for connecting such line to a source of nitrogen for purging and flushing.

The condenser 7 cools and condenses water already removed from the feed, and separates and removes non-condensible gases from the condensate. The bottoms head 175 acts as a vapor/liquid separator. Any air leaking into the vacuum system or gases dissolved in the feed are present at the outlet of the condenser as non-condensibles. The removal of such air and gases through the line 106 is the mechanism by which a high vacuum can be maintained in a major part of the appratus. In this connection, it will be noted that there is a clear path by which to maintain a vacuum between the condenser 7 via line 140 to the separator 4, via line 50 to the heat exchanger 3, via line 49 to the still 5, via line 87 to the mixer 53, and via line 51 and the tubes 46 of the heat exchanger 3.

The non-condensible gases from the condenser 7 flow to the vacuum pump 118 where the gases are compressed from a vacuum of approximately 28" of mercury to a slight positive pressure above atmospheric. The discharge from the vacuum pump 118 flows through the flame arrester 123 to a special burner in the heater 6 where the gases are completely burned and discharged through the stack 107 to the atmosphere.

Briefly, during normal operation and following start-up the process utilizing the above-described apparatus includes the steps of charging the apparatus with chemical to be reclaimed via the guage tank 1 and the feed tank 2, preheating the chemical in the heat exchanger 3, to be mixed, if necessary, with caustic soda and antifoaming agent and then feeding the partially vaporized chemical through line 51 to the mixer 53 where it is mixed with heated bottoms from the still 5 and the heater 6, and, separating the mixture thus produced in the still 5, returning the vapor from the still to the heat exchanger 3, and separating reclaimed chemical (product) in the separator 4. The residence time in the mixer 53, i.e. the mixing time is less than one second. An important step in the process is the heating of the still bottoms in the heater 6, and using the thus heated bottoms to effect separation in the still 5 in a high vacuum and at a temperature of less than 400° F. to avoid decomposition. There is no direct or other heating of the still 5 or the contents thereof. It is worth noting that the still bottoms always contain 5-15% of feed chemical to ensure fluidity of such bottoms.

What we claim is:

1. A continuous process for recovering a purified aqueous solution of a gas treating chemical having a decomposition temperature from a waste aqueous solution of said gas treating chemical containing impurities, comprising the steps of:
    (a) preheating said waste aqueous solution of said gas treating chemical in at least a partial vacuum to partially vaporize the chemical solution in order to produce a product vapor, containing water vapor and some of said gas treating chemical, and a concentrated chemical solution containing water, remaining gas treating chemical and said impurities;
    (b) heating the product vapor and the concentrated chemical solution in a high vacuum of at least 16" mercury to a temperature below said decomposition temperature of the gas treating chemical to further vaporize said remaining gas treating chemical and water from said concentrated solution in order to separate on a continuous basis additional product vapor leaving a residue of the solution of the waste gas treating chemical containing said impurities;
    (c) heating most of said residue separated from the product vapor to a temperature below said decomposition temperature;
    (d) thoroughly mixing said heated residue with said product vapor and said concentrated chemical solution to effect heating step (b); and
    (e) condensing said product vapor produced in steps (a) and (b) in order to recover a purified aqueous solution of said gas treating chemical.

2. A process according to claim 1, wherein said preheating step is effected by placing said product vapor in heat exchange relationship with said waste aqueous solution of said gas treating chemical.

3. A process according to claim 1, including the step of adjusting the pH of the product vapor and the concentrated chemical solution to approximately 8 prior to said heating step (b).

4. A process according to claim 1, wherein the heating of the product vapor and the concentrated chemical solution in step (b) is effected at a temperature of less than 400° F. and a vacuum of from 20 to 29" mercury.

5. A process according to claim 4, wherein said heating of the product vapor and the concentrated chemical solution in step (b) is effected at a temperature of 300° to 390° F.

6. A process for recovering a purified aqueous solution of a gas treating chemical from a waste aqueous solution of said gas treating chemical containing impurities, comprising the steps of:
    (a) preheating said waste aqueous solution of said gas treating chemical in an at least partial vacuum to partially vaporize the chemical solution in order to produce a product vapor, containing water vapor and some of said treating chemical, and a concentrated chemical solution containing water, remaining gas treating chemical and said impurities;
    (b) heating the product vapor and the concentrated chemical solution in a high vacuum of from 20 to 29" mercury at a temperature of less than 400° F. to further vaporize said remaining treating chemical and water from said concentrated solution in order to separate additional product vapor leaving a residue of the waste treating chemical solution;
    (c) heating a portion of the residue;
    (d) mixing said heated residue with said product vapor and said concentrated chemical solution to effect heating step (b); and
    (e) condensing said product vapor produced in steps (a) and (b) in order to recover a purified aqueous solution of said gas treating chemical;
wherein a 5 to 15% content of said gas treating chemical is maintained in the residue heated in step (c) to ensure fluidity of the residue.

7. A process according to claim 4, wherein said mixing step (d) occurs in less than one second.

8. A process according to claim 2, including the step of controlled cooling said product vapor to effect partial condensation thereof and removal of light contaminants to produce a recovered product.

9. A process according to claim 8, wherein said recovered product is filtered to complete the recovery process.

10. A process according to claim 3, wherein said pH is adjusted by adding caustic soda to said product vapor and said concentrated chemical solution immediately prior to said heating step (b).

11. A process according to claim 1 wherein the treating chemical is diethanolamine.

12. A process according to claim 1 wherein the heating of said residue is effected in a heater provided with tubes having tubewalls, by passing said residue through said tubes in such a volume and at such a velocity that layers of said residue immediately adjacent to said tubewalls are heated to a temperature which does not exceed 410° F. while said residue has an outlet temperature of 370°-400° F.

13. A process according to claim 12 wherein said residue is passed through said tubes at a velocity of 6 to 10 feet per second and has a residence time in said tubes of 30-60 seconds.

14. A process according to claim 1 wherein said heated residue, said product vapor and said concentrated chemical solution are mixed in a mixer capable of thoroughly mixing said residue, said product vapor and said concentrated chemical solution in less than one second.

15. A process according to claim 1 wherein a 5 to 15% content of the treating chemical is maintained in the residue to ensure fluidity of said residue.

16. A continuous process for recovering a purified aqueous solution of a gas treating chemical having a decomposition temperature of about 400° F. from a waste solution of said chemical containing impurities, comprising the steps of:
  (a) heating said waste aqueous solution in a high vacuum of at least 16" mercury to a temperature below said decomposition temperature of the treating chemical to vaporize some of said chemical solution to produce a product vapor, containing said treating chemical and water vapor, and unvaporized residue;
  (b) separating said product vapor from said residue;
  (c) separating most of said residue from a remainder of said residue, discharging said remainder and heating said most of said residue to a temperature less than but approaching said decomposition temperature while avoiding localized overheating and decomposition of said residue;
  (d) thoroughly and rapidly mixing said heated residue with said chemical solution to effect heating step (a); and
  (e) condensing said separated product vapor from step (b) to provide a recovered purified aqueous solution of said gas treating chemical.

* * * * *